(12) United States Patent
Slee et al.

(10) Patent No.: US 12,702,838 B2
(45) Date of Patent: Aug. 11, 2026

(54) MULTI-ELECTRODE SPINAL CORD STIMULATION THERAPY

(71) Applicant: BIOTRONIK SE & Co. KG, Berlin (DE)

(72) Inventors: Sean Slee, Tigard, OR (US); Andrew B. Kibler, Lake Oswego, OR (US); Marcelo Baru, Taulatin, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 361 days.

(21) Appl. No.: 18/285,160

(22) PCT Filed: Mar. 10, 2022

(86) PCT No.: PCT/EP2022/056190

§ 371 (c)(1),
(2) Date: Sep. 29, 2023

(87) PCT Pub. No.: WO2022/207269

PCT Pub. Date: Oct. 6, 2022

(65) Prior Publication Data

US 2024/0207616 A1 Jun. 27, 2024

Related U.S. Application Data

(60) Provisional application No. 63/168,604, filed on Mar. 31, 2021.

(30) Foreign Application Priority Data

Apr. 29, 2021 (EP) .................................... 21171279

(51) Int. Cl.
*A61N 1/05* (2006.01)
*A61N 1/36* (2006.01)

(52) U.S. Cl.
CPC ....... *A61N 1/36139* (2013.01); *A61N 1/0553* (2013.01); *A61N 1/36157* (2013.01)

(58) Field of Classification Search
CPC .............. A61N 1/36139; A61N 1/0553; A61N 1/36157; A61N 1/0551; A61N 1/36142;
(Continued)

(56) References Cited

U.S. PATENT DOCUMENTS 8,874,219 B2 10/2014 Trier et al.
2017/0259065 A1 9/2017 Baru et al.
(Continued)

FOREIGN PATENT DOCUMENTS

EP 2958619 A2 12/2015
EP 3381507 A1 10/2018
(Continued)

OTHER PUBLICATIONS

International Search Report and Written Opinion for PCT/EP2022/056190, mailed May 19, 2022, 3 pages.

*Primary Examiner* — Benjamin J Klein
*Assistant Examiner* — Alisha J Sircar
(74) *Attorney, Agent, or Firm* — FBT GIBBONS LLP

(57) ABSTRACT

A device used for neurostimulation includes a plurality of electrodes. In order to improve therapeutic efficacy when using a group of N electrodes equal to or larger than 3, the device is configured to deliver a number of N+1 electrical phases during one cycle via the electrodes such that during N electrical phases of the cycle each electrode of the group delivers alternating a therapeutic electric phase and a number of N−1 charge balancing electric phases. One electrode of the group delivers its specific therapeutic electric phase and the other electrodes of the group deliver a charge balancing phase having an opposite polarity of the therapeutic electric phase delivered, and such that during an
(Continued)

Figure 1:
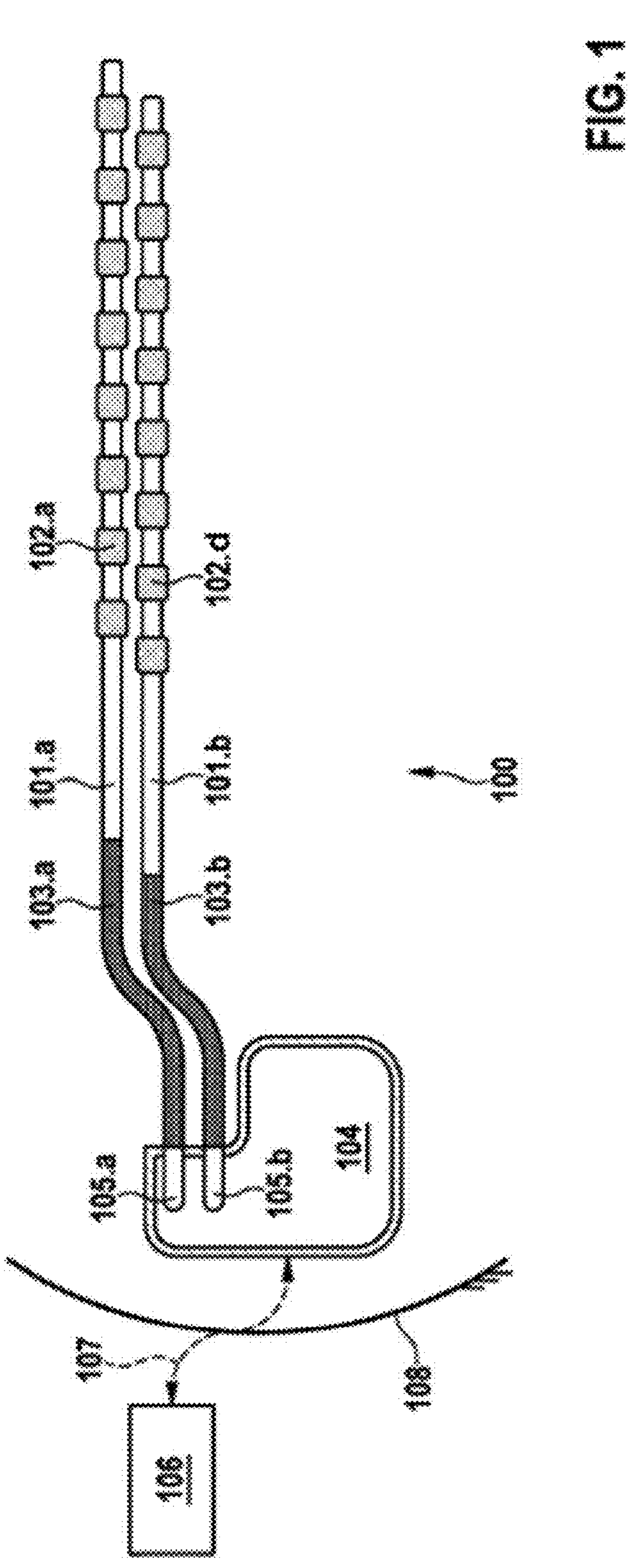

additional electrical phase each electrode of the plurality of electrodes delivers an electrical phase with an amplitude that establishes charge neutrality for residual charge on each respective electrode based on phases of the N other electrical.

20 Claims, 11 Drawing Sheets

(58) Field of Classification Search
CPC .............. A61N 1/3615; A61N 1/36164; A61N 1/36062; A61B 5/388; A61B 5/1118; A61B 5/4836; A61B 5/686
See application file for complete search history.

(56) References Cited

U.S. PATENT DOCUMENTS

| | | | | |
|---|---|---|---|---|
| 2018/0272124 | A1* | 9/2018 | Kibler | A61N 1/025 |
| 2019/0175904 | A1* | 6/2019 | Baru | A61N 1/0551 |
| 2019/0329039 | A1* | 10/2019 | Marnfeldt | A61N 1/36164 |
| 2020/0376272 | A1* | 12/2020 | Block | A61N 1/36071 |

FOREIGN PATENT DOCUMENTS

| | | | |
|---|---|---|---|
| EP | 3791923 | A1 | 3/2021 |
| WO | WO 2014/134075 | A1 | 9/2023 |

* cited by examiner

MULTI-ELECTRODE SPINAL CORD STIMULATION THERAPY

The invention is directed to a device for neurostimulation and a respective method.

Neurostimulation devices are used to deliver electrical stimulation therapy to a patient's body to various tissue sites to treat a variety of symptoms or conditions such as chronic pain, Parkinson's disease, epilepsy, urinary or fecal incontinence, sexual dysfunction, obesity or gastroparesis. Such devices usually deliver electrical stimulation therapy via one or more leads that comprise electrodes located proximate to target locations associated with the brain, the spinal cord, pelvic nerves, peripheral nerves, or the gastrointestinal tract of the patient. Hence, electrical simulation may be used in different therapeutic applications, such as deep brain stimulation (DBS), spinal cord stimulation (SCS), pelvic stimulation, gastric stimulation, or peripheral nerve stimulation (PNS).

Spinal cord stimulation (SCS), as a means of pain relief for patients suffering from neuropathic pain, has traditionally been thought of as requiring paresthesia sensations to overlap a patient's region of pain in order to provide relief. Recent research has shown that an alternate paresthesia-free mechanism of pain relief is available through higher frequency (compared to traditional tens of Hz) stimulation which is effective in patients without requiring intra-operative electrode mapped selection.

In the last few years, therapies have demonstrated efficacy of a paresthesia-free method of pain relief whereby the patient does not experience paresthesia and the stimulation electrodes selected may not map directly to a dermatomal alignment with the patient's region of pain. High-frequency SCS therapy utilizes stimulation frequencies between 1.5 kHz and 100 KHz, preferred 10 kHz, to achieve a neuromodulatory effect without recruiting the dorsal column fibers associated with paresthesia. Research indicates that this therapy modality reduces the wind-up hypersensitivity of dorsal horn interneurons responsible for relaying a painful sensation from the peripheral to the central nervous system. Pain relief associated with this stimulation may require several hours to a day to take effect.

The mechanism of action of this mode of therapy is still under debate; however: the prevailing theory is as follows. High-frequency SCS stimulation has little influence on the dorsal column axons which facilitate paresthesia therapy, instead directly inducing slight potentiation changes on lamina I neurons in the dorsal horn of the spinal cord. The potentiation changes trigger a cascade of intracellular signalling responses which induce a direct inhibition of sensitization and suppression of activity of neuropathic pain relay neurons in the dorsal horn.

This paresthesia-free SCS approach is similar in frequencies to high-frequency transcutaneous spinal electroanalgesia (TSE) which has been available for decades. Whether the underlying mechanisms and site of pain relief action are, the same between high-frequency TSE and high-frequency SCS remains to be determined.

Drawbacks of 10,000 Hz stimulation are as follows: it requires very high frequency stimulation control, energy is wasted through parasitic capacitive charge and discharge as a result of frequent polarity transitions of current delivery, and most important neuronal response is not efficient at 10,000 Hz stimulation frequency given the anodic pulse amplitude is constrained by timing to be the same as the cathodic pulse amplitude, which in turn influences cathodic stimulation thresholds. The consequences of a high-energy SCS implantable device include frequent recharging and large device size, both of which can have a significantly negative patient impact. The number of recharge cycles is also limited requiring the patient to have more frequent revision surgeries for device replacement.

U.S. Pat. No. 10,870,000 B2 describes a paresthesia-free SCS approach which is able to achieve efficient paresthesia-free pain relief with stimulation frequencies below or equal to 1,500 Hz by utilizing a stimulation charge-balancing approach. This approach utilizes multiple electrodes to provide charge-balanced stimulation which delivers pain relieving neuromodulation at high frequencies and with lower energy requirements compared to the previously known methods. This is because in the waveform disclosed in this prior art, the distributed balance phase does not influence the stimulating phase threshold. The mentioned prior art describes several methods for delivering stimulation via multiple electrodes across location and time using an amplitude that is constant across therapeutic electrodes, or different but charge balanced in an interdependent manner. This results in limited therapeutic amplitude control which is not ideal for many patients.

Accordingly, there is a desire to provide a device for neurostimulation with improved therapeutic efficacy when using a plurality of electrodes in the sub-perception window. Accordingly, a respective method for neurostimulation is needed.

The above object is solved by a device for neurostimulation of a patient's body with the features of claim 1 and the respective method with the features of claim 7.

In particular, the above object is solved by a device for neurostimulation of a patient's body, wherein the device comprises a plurality of electrodes, wherein the number of the plurality of electrodes is Z, wherein a group of N electrodes of the plurality of electrodes (N less than or equal to Z) is equal to or larger than 3, wherein the device is configured to deliver a number of N+1 electrical phases during one cycle via the plurality of electrodes

- such that during N electrical phases of the cycle each electrode of the group delivers alternating a therapeutic electric phase and a number of N−1 charge balancing electric phases, wherein the therapeutic electric phase of one electrode has an amplitude I1, I2, . . . IN specific to this electrode, wherein during a time of one phase one electrode of the group delivers its specific therapeutic electric phase and the other electrodes of the group or of the plurality of electrodes deliver a charge balancing phase having a polarity being opposite to the polarity of the specific therapeutic electric phase delivered at the same time, and
- such that during an additional electrical phase each electrode of the plurality of electrodes delivers an electrical phase with an amplitude that establishes charge neutrality for residual charge on each respective electrode based on phases of the N other electrical phases, e.g. electrical phases of the same electrode.

The above neurostimulation device comprises a plurality of Z electrodes, wherein all or a (sub-)group of N (N is less than or equal to Z) electrodes of these electrodes is used for delivery of a therapeutic electric phase. N is equal to or larger than 3. The neurostimulation therapy is delivered in cycles, wherein each cycle has a number of N+1 electrical phases. The plurality of electrodes may be located at a distal portion of at least one percutaneous lead implantable in vicinity of a target for stimulation within the patient's body. Alternatively, the lead may be a paddle lead or any other type of lead for neurostimulation. The device may further comprise a pulse generator which may be implantable. The pulse generator comprises a connection module for electrically connecting the at least one lead to its electrical circuitry. The pulse generator comprises the electrical circuitry, for example comprising an application specific integrated circuit (ASIC), for providing stimulation output and a power supply such as a battery, wherein the electrical circuitry, the power supply and the at least one lead with the electrodes are electrically interconnected with each other. The pulse generator may comprise a processor and/or a memory for storing data and/or a communication module for communication with an external computer. The processor, memory and/or communication module may be electrically interconnected with the electrical circuitry, the power supply and the at least one lead. All elements of the pulse generator are contained within a hermetically sealed housing.

The group of N electrodes of the plurality of electrodes can also be or be called a subset of electrodes of the plurality of electrodes.

According to the invention, the N+1 electrical phases of one cycle consist of N electrical phases during which the therapeutic electrical phases by the group of electrodes are delivered to the patient's body (with concurrent charge balancing phases) and one additional electrical phase during which a residual charge balancing phase is delivered. During the additional electrical phase each electrode or a subset of the plurality of electrodes delivers an electrical phase with an amplitude that establishes charge neutrality for residual charge on each respective electrode based on delivered or to be delivered phases of the N other electrical phases. Thereby accurate charge balancing on each electrode is provided, in particular, if—as in the inventive device—one specific amplitude I1, I2, . . . IN is used for the therapeutic electric phase of each electrode of the group. During the N electrical phases of the cycle each electrode of the group delivers alternating the therapeutic electric phase with its specific amplitude I1, I2, . . . IN and a number of N−1 charge balancing electric phases, wherein during a time of one phase one electrode of the group delivers its specific therapeutic electric phase and the other electrodes of the group deliver a charge balancing phase having a polarity being opposite to the polarity of the specific therapeutic electric phase delivered at the same time.

In contrast to this, the amplitude of the "Rotating Electrodes" therapy disclosed in the prior art U.S. Pat. No. 10,870,000 B2 is programmed using a fraction of the perception threshold (PT), e.g. 50%. In clinical practice this results in the therapeutic electrode with the lowest threshold determining the amplitude for the whole group of electrodes in the pattern. This may result in sub-optimal therapeutic amplitudes at active electrodes with higher thresholds. Further, the Rotating Electrodes therapy of the above-mentioned prior art document utilizes multiple electrodes to provide cathodically or anodically-weighted, charge-balanced stimulation whereby the stimulation return currents and charge balancing occurs at the same time and in a distributed fashion. However, the spatio-temporal pattern of stimulation and charge balancing complicates the use of variable amplitudes across electrodes.

The present disclosure describes a multi-phase therapy with independent variable amplitudes across electrodes while retaining efficient charge balancing on each active electrode. In order to enable independent amplitude settings for each therapeutic electric phase, it is proposed to add the additional phase to the collection of pulses, a so-called "residual charge balancing" phase which may be carried out at the end of a complete stimulation cycle of therapeutic electric phases. Alternatively, the residual charge balancing phase may be delivered at one phase between two cycles providing therapeutic electric phases. During each therapeutic electric phase, return currents are still shared among active electrodes of the group or of the plurality of electrodes or a subset of the plurality of electrodes, and at the residual charge balancing phase of stimulation, a balancing current is shared between active electrodes equal to the unbalanced charge remaining on each electrode divided by the duration of the charge balancing phase. The charge balancing phase may be active or passive, or a combination of the two.

The integrated average charge delivered by the therapeutic electric phases and charge balancing phases (including the additional phase for residual charge balancing) is zero over time.

In one embodiment, the device provides periodic passive balance between all participating electrodes of the group of electrodes or a subset of the plurality of electrodes or the plurality of all electrodes in order to prevent voltage runaway in the effective series capacitance of the stimulation path. In one embodiment the charge balancing electric phases for charge balancing in one phase have in sum the same amount of charge as the respective therapeutic electric phase.

In one embodiment the device is configured to deliver the therapeutic electric phases and charge balancing electric phases (including the additional phase for residual charge balancing) such that the therapeutic electric phases and the charge balancing phases are separated by inter-phase intervals. The frequency of the cycles may be below or equal to 1,500 Hz, in a further embodiment between 1,000 Hz and 1,500 Hz. In one embodiment the amplitude of the therapeutic phases is in the range from 1.0 mA to 20.0 mA, in a further embodiment in the range from 1.0 mA to 5.0 mA. Electrodes of the group deliver the therapeutic electric phase, wherein the therapeutic electric phase may be anodic or cathodic in nature. Further, the stimulation waveform may employ pulse width modulation of the therapeutic electric phases and/or charge balancing phases for stimulation focus control.

An electric phase can also be or be called an electric pulse.

In one embodiment the device may be configured such that amount of the amplitudes of the charge balancing electric phases is the (N−1)th part or the (Z−1)th part of the amount of the specific amplitude of the specific therapeutic electric pulse delivered at the same time during one of the N therapeutic electrical pulses. In this embodiment the charge balancing electric phases are equally shared between the electrodes of the group or of the plurality of electrodes of which some do not deliver a therapeutic electric phase. Other distribution of charge balancing electric phases across these electrodes is possible, as well.

Figure 12:
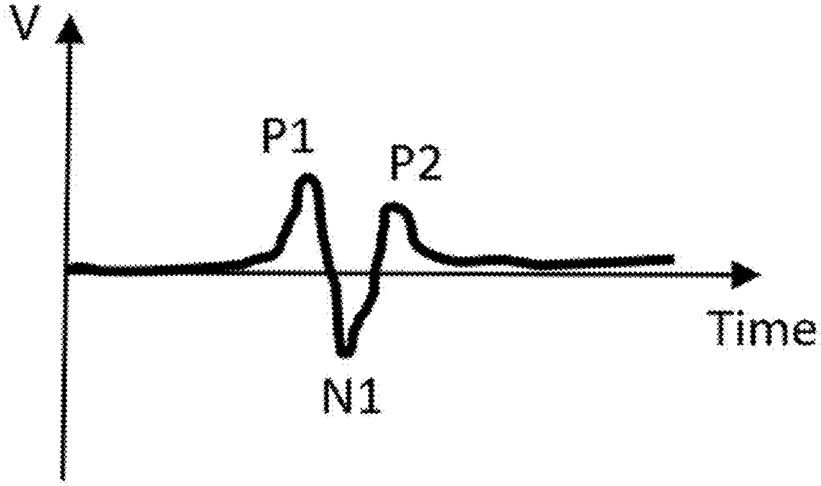

In one embodiment, in particular for use outside of a clinic, the device may be configured such that the amplitude of the specific therapeutic electric phase of each electrode of the group is automatically adjusted using measurement of recorded evoked compound action potential (ECAP) waveform. The measurement results are used to determine activation thresholds and thereby the specific therapeutic electric phase amplitude for the respective electrode. Further, in this case the device may be configured such that ECAP waveform measurement is provided using at least one auxiliary electrode of the plurality of electrodes different from the group of electrodes. Furthermore, the device may be configured such that the ECAP waveform measurement is provided in predefined time intervals and/or if the patient's body position and/or activity change is detected, for example by using an accelerometer contained within the device. Beyond manual programming, a preferred method of neurostimulation is thereby provided which enables periodic automatic adjustments of amplitude employs closed-loop stimulation. ECAPs are recorded, for example from dorsal column fibers, while therapy is delivered (leveraging on the embodiments described in U.S. Pat. No. 10,842,996 B2) and individual therapeutic electric phase amplitudes may be adjusted to maintain the sensed ECAPs amplitudes within a therapeutic sub-perception window. This sub-perception window is typically only up to approximately 10 μV in amplitude, when stimulating with tens of Hz frequencies, whereas the perception window typically extends to less than 35 μV. Any generated ECAP amplitude above 35 μV is associated with intolerable stimulation for the patient. This may be patient dependent though and may require calibration to adjust the amplitudes. The ECAP amplitude is defined as the voltage difference between the second positive peak P2 and the negative peak P1 as shown in FIG. 12.

In one embodiment the device may be configured such that for assessing the amplitude of the specific therapeutic electric phase of each electrode of the group the specific activation threshold for each electrode is determined, wherein the amplitude of one specific electrode of the group is a pre-defined part of the measured specific activation threshold of this electrode. The 'perception threshold' or 'activation threshold' refers to the stimulation amplitude which is just strong enough to induce action potentials (e.g. neural response threshold, ECAP amplitude in the perception window as described before). Previous reports in prior art demonstrate that action potential thresholds typically coincide with perception threshold. Furthermore, action potentials generation is a pre-requisite for recording ECAPs. The device may be configured such that the determination of the specific activation threshold of each electrode of the group may comprise in a first step a rough titration by ramping the therapeutic electric phase amplitudes up on all N electrodes of the group simultaneously until the activation threshold is reached at one electrode. Then, the therapeutic phase amplitude on all N electrodes is reduced until below this activation threshold. Afterwards, for each electrode of the group the amplitude is increased separately in order to detect the specific activation threshold of each electrode of the group. For sub-perception therapy the stimulation amplitude of the therapeutic electric phase is programmed to a pre-defined part of 40% to 60%, for example 50%, of the determined activation threshold on each electrode. The above procedure may be repeated for different activity changes or positions of the patient's body.

In a further embodiment, during any of the N+1 phases, the device casing sources or sinks current to provide balance to the net currents of the active electrodes.

The object is further solved by a method for neurostimulation of a patient's body using a plurality of electrodes, wherein the number of the plurality of electrodes is Z, wherein a group of N electrodes of the plurality of electrodes (N less than or equal to Z) is equal to or larger than 3 having the above-mentioned advantages and embodiments. Further, a number of N+1 electrical phases during one cycle via the plurality of electrodes is delivered wherein during N electrical phases of the cycle each electrode of the group delivers alternating a therapeutic electric phase and a number of N−1 charge balancing electric phases, wherein the therapeutic electric phase of one electrode has an amplitude I1, I2, . . . IN specific to this electrode, wherein during a time of one phase one electrode of the group delivers its specific therapeutic electric phase and the other electrodes of the group or a subset of the plurality of electrodes or the plurality of electrodes deliver a charge balancing phase having a polarity being opposite to the polarity of the specific therapeutic electric phase delivered at the same time, and wherein during an additional electrical phase the N electrodes and possibly a subset of electrodes of the plurality of electrodes or the plurality of electrodes deliver electrical charge with an amplitude that establishes charge neutrality for residual charge on each respective electrode based on phases of the N other electrical phases, e.g. electrical phases of the same electrode.

In one embodiment of the method the amount of the amplitudes of the charge balancing electric phases may be the (N−1)th part of the amount of the specific amplitude of the specific therapeutic electric phase delivered at the same time during one of the N therapeutic electrical phases.

In one embodiment of the method the amplitude of the specific therapeutic phase of each electrode of the group may be automatically adjusted using ECAP waveform measurement. Furthermore, in one embodiment of the method the ECAP waveform measurement is provided using at least one auxiliary electrode of the plurality of electrodes Z different from the group of electrodes N. Further, in one embodiment the ECAP waveform measurement is provided in predefined time intervals and/or if the patient's body position and/or activity change is detected, for example by using an accelerometer contained within the device.

In one embodiment of the method, for assessing the amplitude of the specific therapeutic phase of each electrode of the group the specific activation threshold for each electrode is determined, wherein the amplitude of one specific electrode of the group is a pre-defined part of the measured specific activation threshold of this electrode.

The above device or method may particularly be used for SCS, but DBS, pelvic stimulation, gastric stimulation, or peripheral nerve stimulation (PNS) may be provided with the above device or method, as well.

The above device and method provide multi-phase neurostimulation therapy with combined single residual charge balance phase. Further, in embodiments clinical and closed-loop titration workflows utilizing independent electrode amplitudes are proposed, wherein the closed-loop titration may be ECAP-based differential closed-loop titration of therapy phases.

Figure 2:
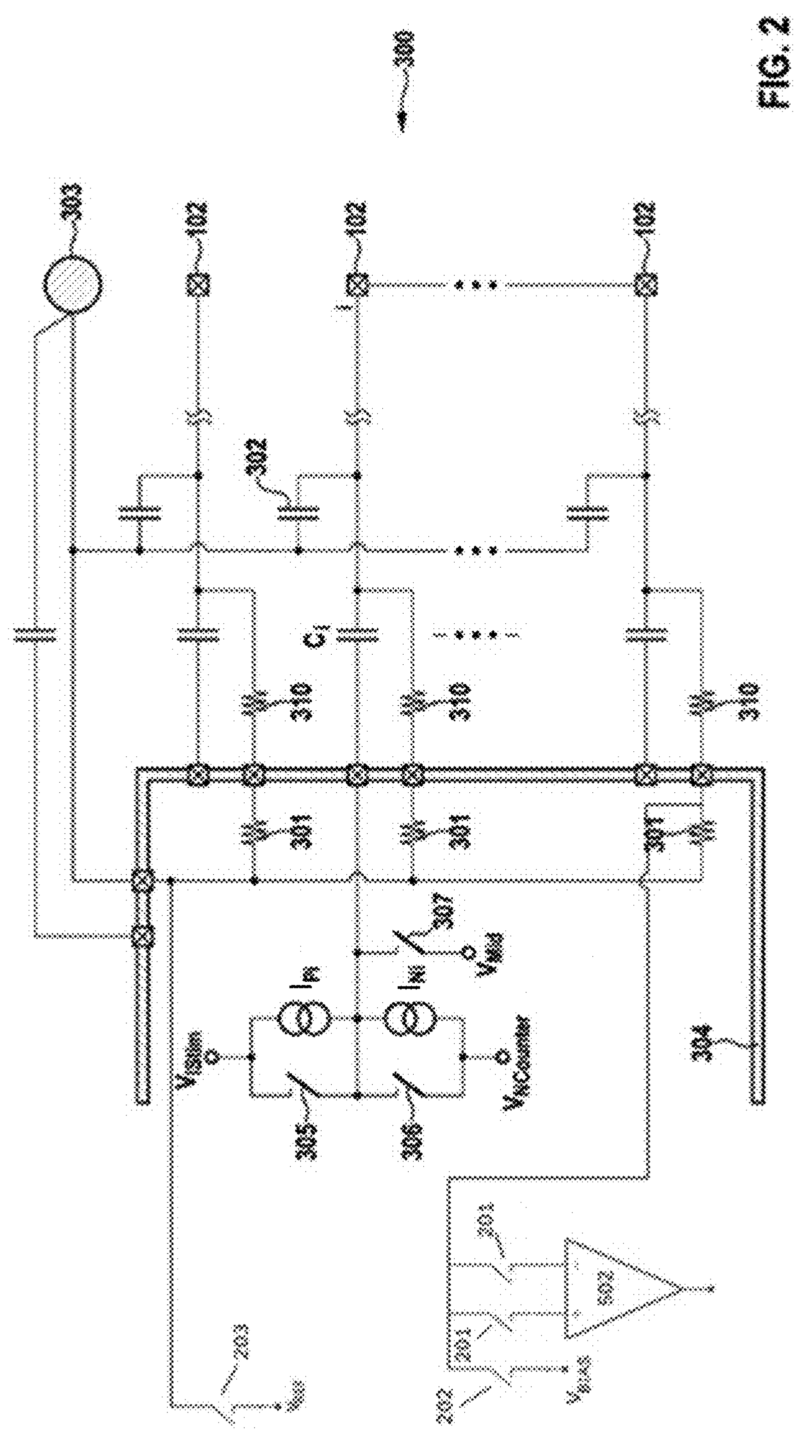
Figure 3:
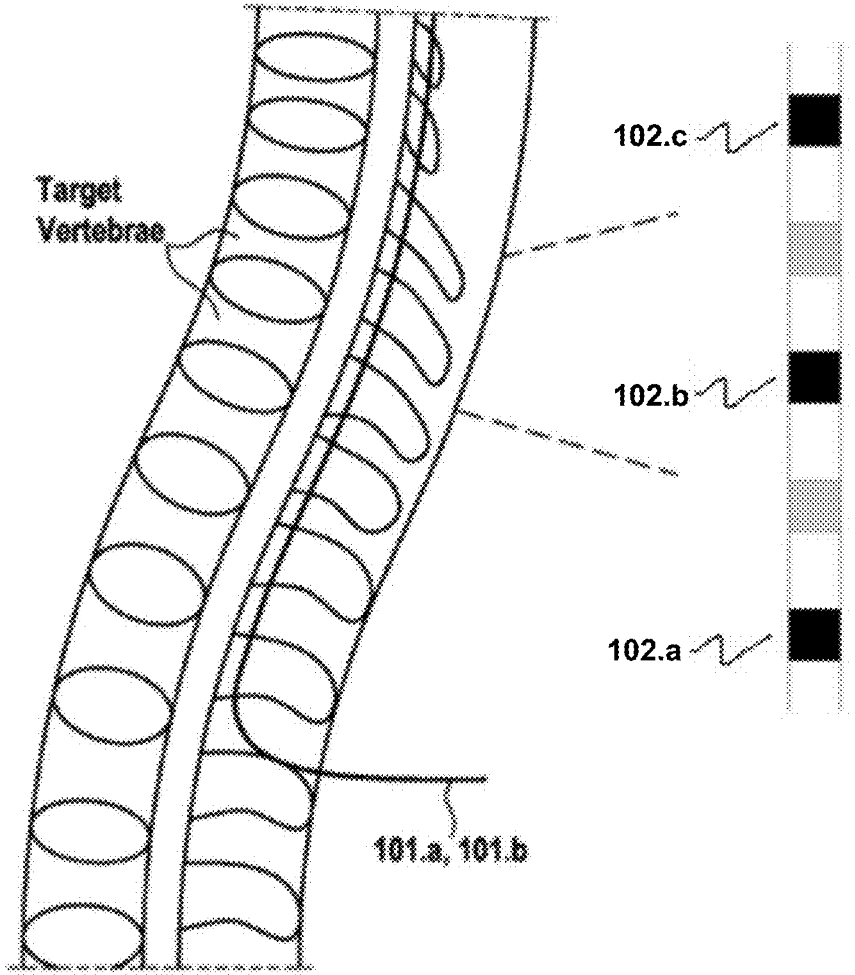
Figure 4:
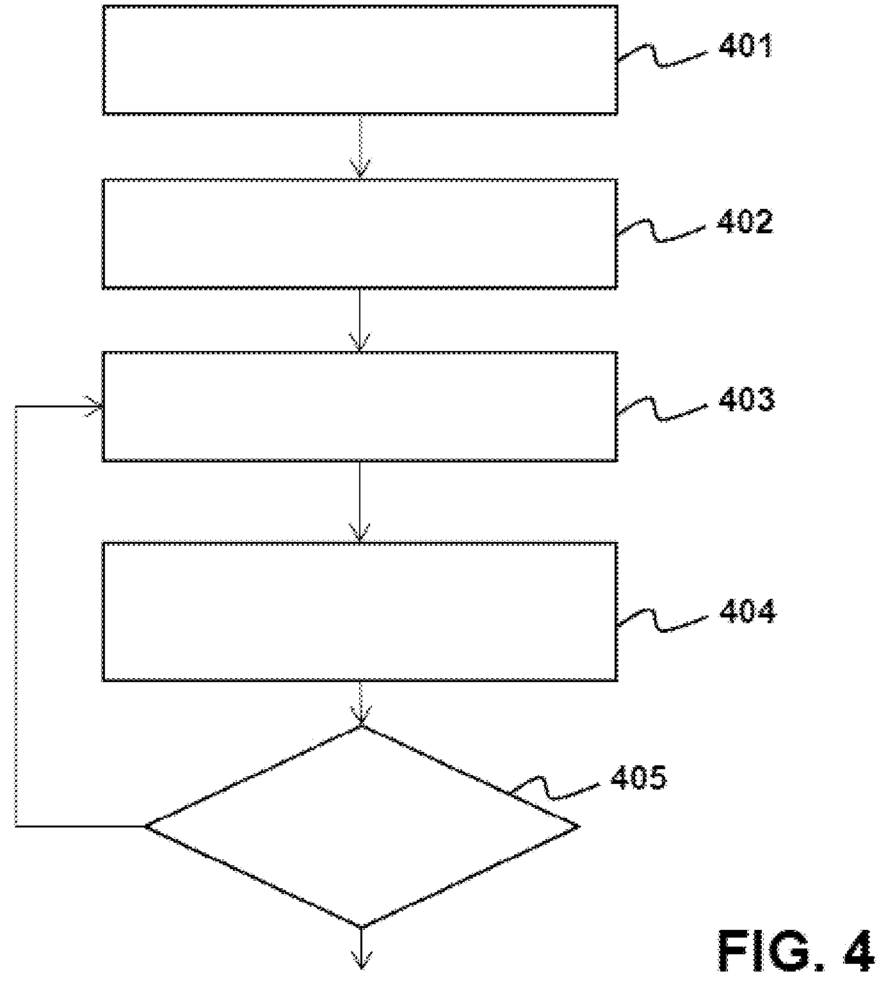
Figure 5:
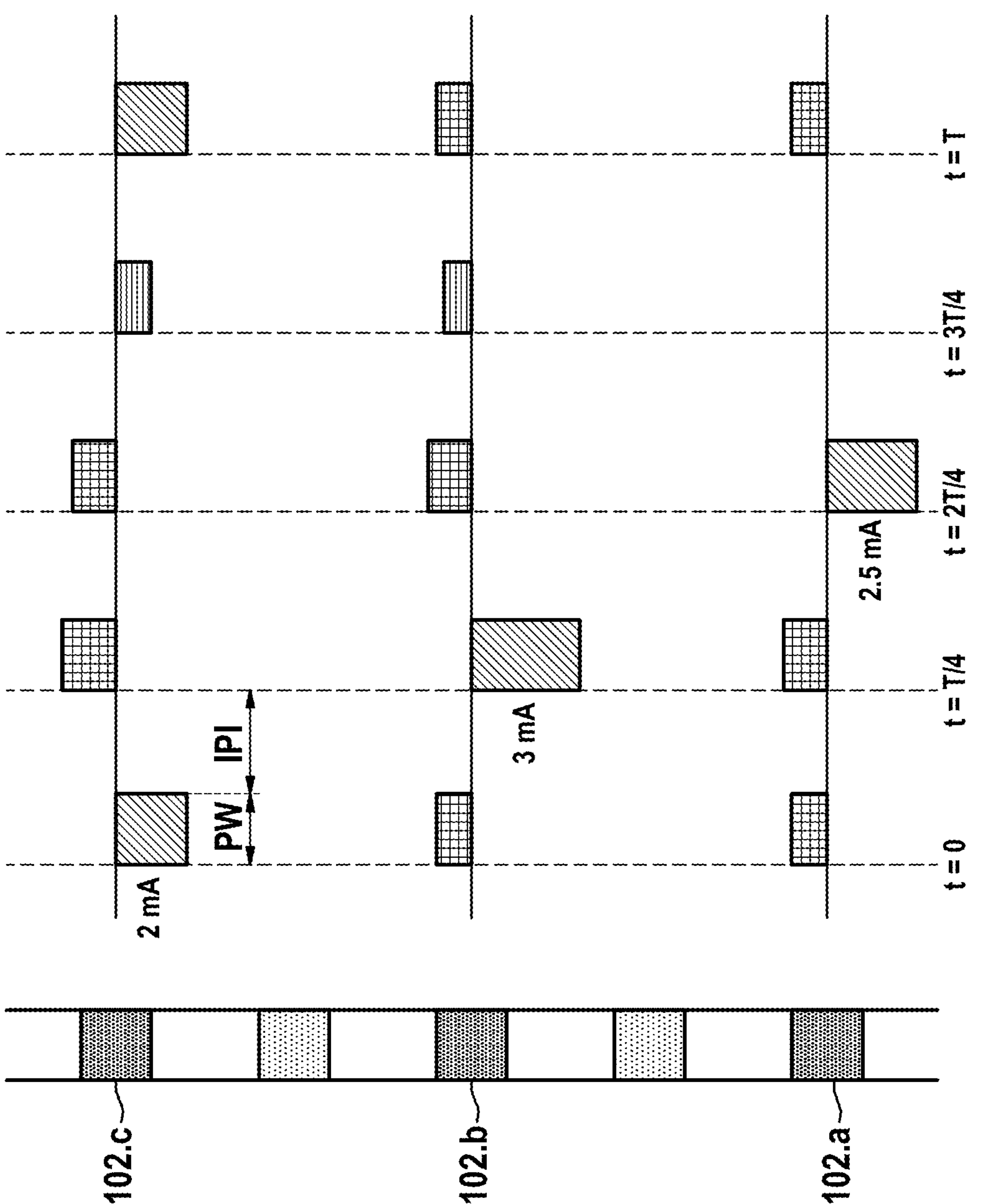
Figure 6:
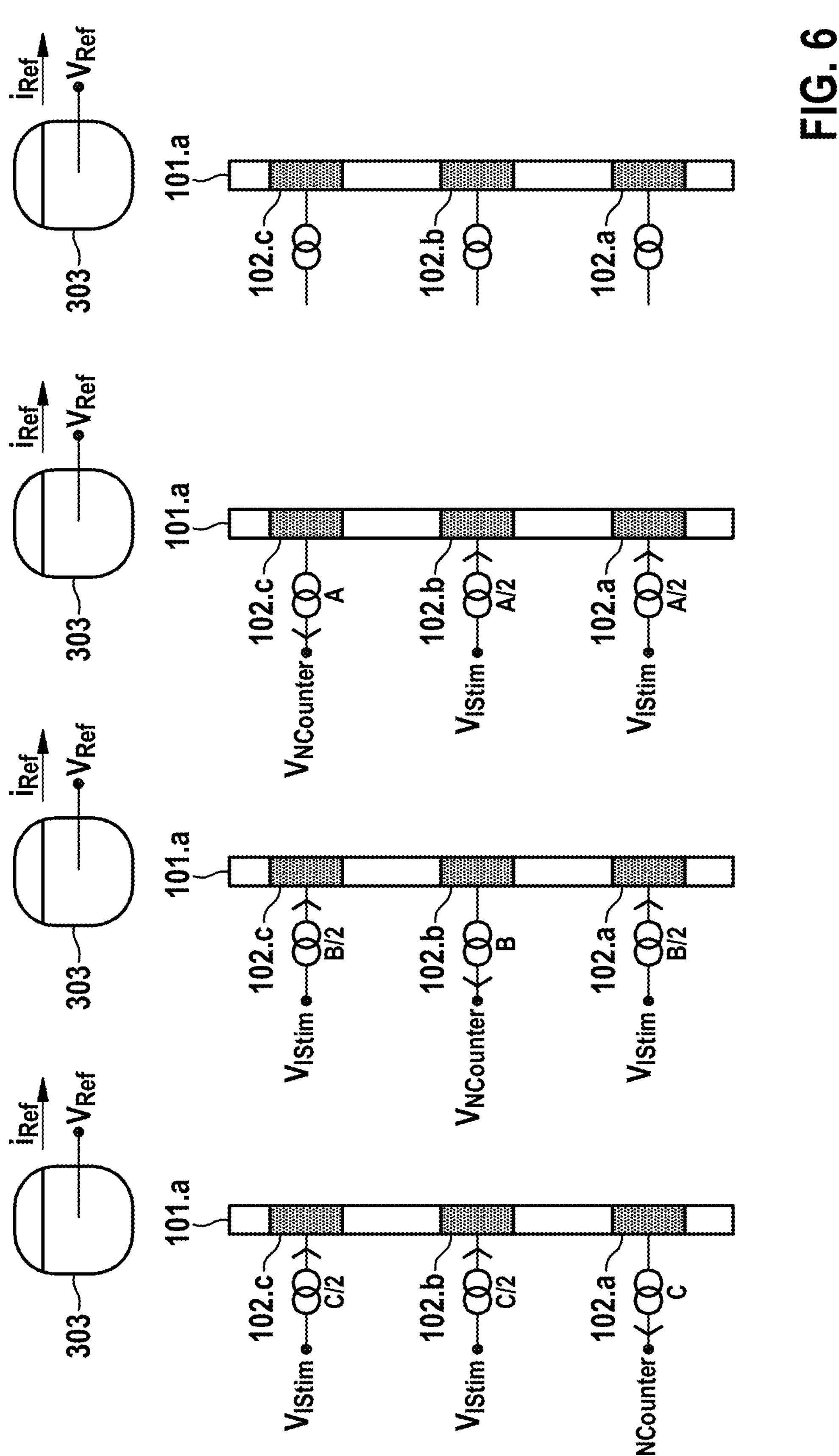
Figure 7:
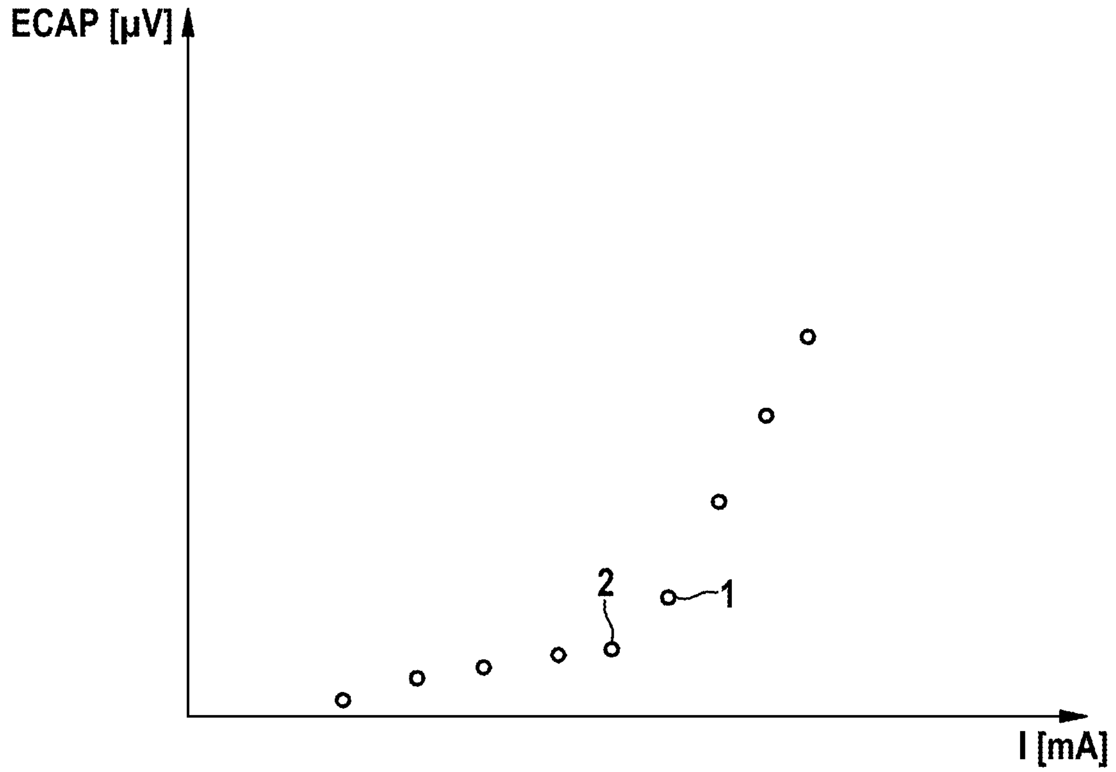
Figure 8:
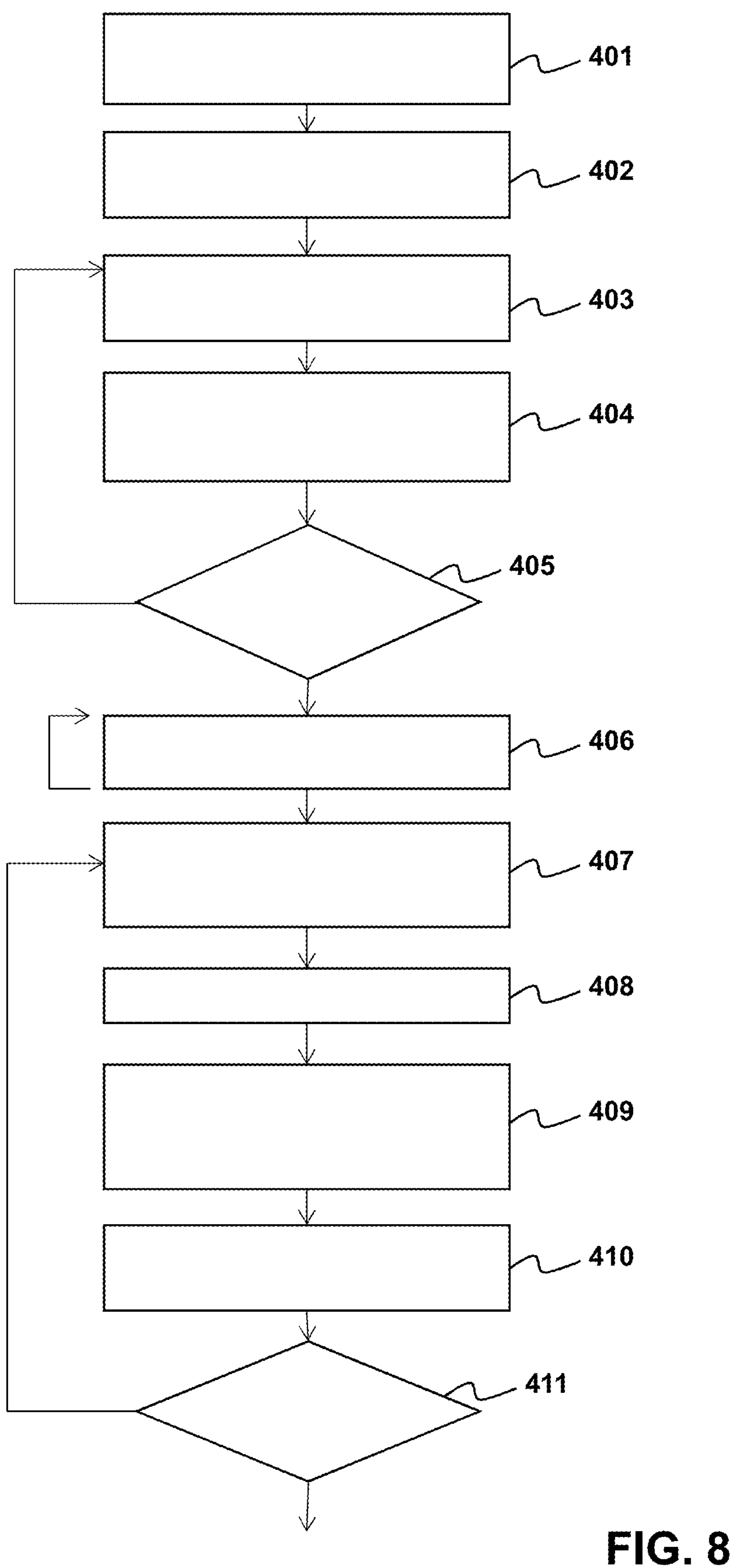
Figure 9:
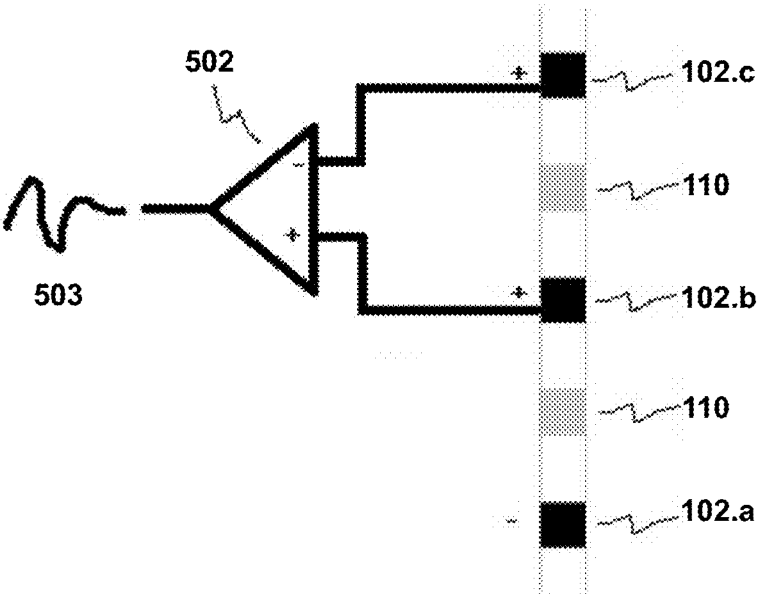
Figure 10:
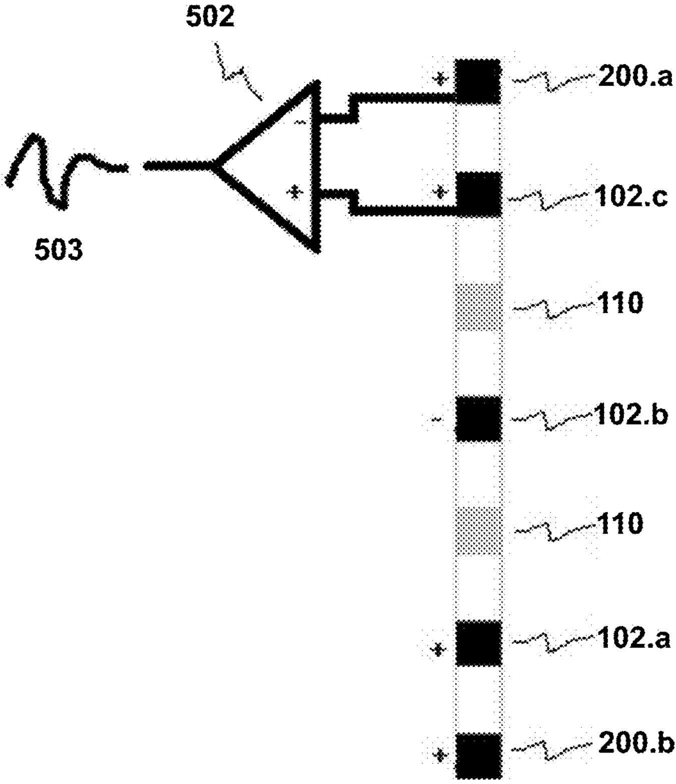
Figure 11:
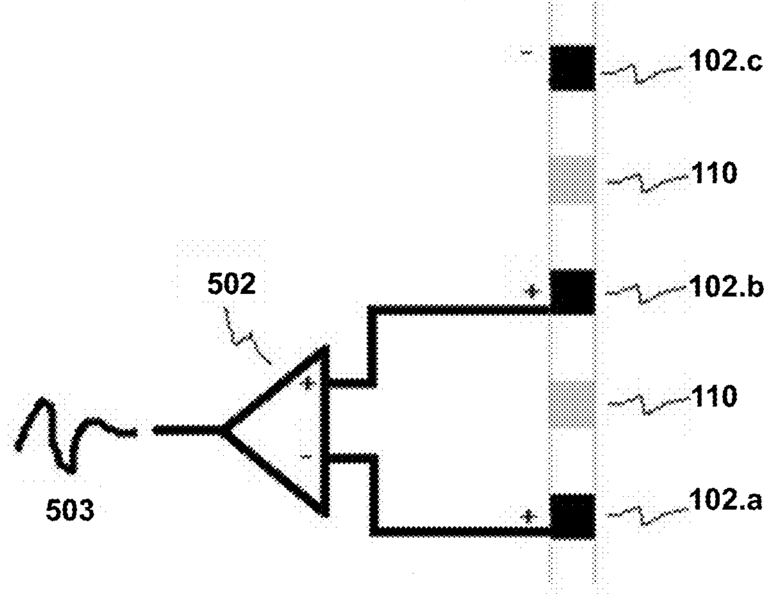

Furthermore, detailed embodiments and features of the present invention will be described below with reference to schematic drawings, wherein FIG. 1 shows an embodiment of a neurostimulation device within a patient's body being part of a SCS implantable system, FIG. 2 shows a wiring diagram of an implantable pulse generator (IPG) front-end for SCS, FIG. 3 shows an example of positioned electrodes for SCS-therapy delivery using the novel multi-phase stimulation waveform for chronic back and leg pain, FIG. 4 depicts a flow diagram of a titration method for specific amplitudes for therapeutic electric phases for different electrodes, FIG. 5 shows an embodiment of one cycle of period T of the neurostimulation method with 3 electrodes (amplitudes vs. time), FIG. 6 depicts the embodiment of FIG. 5 differently, namely showing the utilization of an auxiliary electrode to deliver therapy, FIG. 7 shows an activation signal plot, i.e. the ECAP amplitude vs. the therapeutic electric phase amplitude, FIG. 8 depicts a flow diagram of an automatic titration method for specific amplitudes for therapeutic electric phases for different electrodes using ECAP waveform determination combined with the flow diagram of FIG. 4, FIG. 9-11 show ECAP recording configurations during SCS therapy for different times during one cycle of a neurostimulation device wherein the group contains 3 electrodes and a subset of the plurality of electrodes contains 5 electrodes, wherein in FIG. 9 the bottom electrode 102.*a* delivers the therapeutic electric phase, in FIG. 10 the middle electrode 102.*b* delivers the therapeutic electric phase and in FIG. 11 the upper electrode 102.*c* delivers the therapeutic electric phase.

FIG. 12 shows the voltage difference between the second positive peak P2 and the negative peak P1, defined as ECAP amplitude.

FIG. 1 illustrates an example of an implantable device 100 for spinal cord stimulation (SCS) as one example of a neurostimulation device. Such system includes first and second implantable percutaneous leads 101.*a* and 101.*b* that are implanted into a targeted location in the epidural space. Such lead may be replaced by a paddle lead or other type of SCS lead.

The distal portion of the leads 101.*a* and 101.*b* incorporate a plurality of electrodes 102.*a* and 102.*d* respectively. Octal percutaneous leads 101.*a* and 101.*b* (i.e. each lead has eight electrodes) are shown in the example illustrated in FIG. 1. Each electrode 102.*a*, 102.*d* is connected to an insulated wire (not shown) that run inside flexible insulated carriers 103.*a* and 103.*b*. These carriers 103 get tunnelled during implantation to the vicinity of the implantable pulse generator (IPG) 104 that is typically implanted subcutaneously in the patient's lower abdominal or gluteal region. Carriers 103.*a* and 103.*b* terminate proximally in connectors 105.*a* and 105.*b* respectively that are then inserted into the header of the IPG 104 to allow conducting electrical charge to electrodes 102.*a*, 102.*d*.

The IPG 104 may communicate with one external device 106 through suitable radio frequency (RF, e.g. MICS-band or low-energy Bluetooth®) or an inductive link 107 through the patient's skin 108. The external device 106 may include a computer such as clinician programmer or a patient remote, or an external charger among others. An external charger may send power transcutaneously though an inductive link 107 for battery recharge if the IPG 104 is powered by a secondary battery.

The electrodes 102.*a*, 102.*d* (in the following electrodes 102) are electrically driven by a front-end 300 which is located in the IPG 104. The front-end 300 is shown in FIG. 2. Component $C_i$ represents the DC blocking capacitor in series with each of the electrodes 102 with the number i traditionally employed to deliver electrical stimulation.

Resistors 301 in FIG. 2 are bleeding resistors (hundreds of kΩ), placed in star configuration, typically utilized in IPG's front-end 300 for passive charge neutrality. Capacitors 302, also in star configuration, provide filtering against electromagnetic interference (transitory voltage suppression protections, such as against external defibrillation pulses and electrostatic discharges, are not shown). The common node of both resistors 301 and capacitors 302 star configurations are connected to the conductive area 303 of the case of IPG 104.

An application specific integrated circuit (ASIC) 304 provides five controllable elements for biphasic stimulation where only one may be active at any time when the respective electrode 102 is utilized for therapy delivery. Current $I_{pi}$ permits sourcing current through an electrode 102 from the programmable voltage $V_{IStim}$ whereas current $I_{Ni}$ permits sinking current to a programmable voltage $V_{NCounter}$, which may be system ground $V_{SS}$, as desired. Having sourcing and sinking currents independently controllable at each electrode 102 (shown only for one electrode 102) permits delivering simultaneous multi-electrode SCS therapy with active charge balancing. Analog switches 305, 306 permit connecting an electrode 102 to either $V_{IStim}$ or $V_{NCounter}$, respectively, when currents of only one type are to be applied. Analog switches 307, referenced to a mid-voltage $V_{Mid}$, permit passive charge balancing. Voltage $V_{Mid}$ may be any voltage between $V_{IStim}$ and $V_{SS}$ including them. Resistors 310 may be added to limit the current in the presence of externally-generated fields (e.g. defibrillation).

Analog switches 201 permit connecting any electrode 102 (shown only for one electrode 102) to an ECAP recording front-end 502. Electrodes 102 can also be connected to a low-noise DC voltage $V_{BIAS}$ during ECAP recording via analog switches 202 to fix a common mode voltage for recording. Embodiments for ECAP recording are further disclosed in U.S. Pat. No. 10,183,168 B2.

The IPG 104 of the embodiment is capable of delivering multi-modality SCS therapy as explained in the following.

FIG. 4 shows one embodiment of a clinical flow diagram of titration method for use with independent therapeutic electric phase/therapeutic electric pulse (TEP) amplitudes. In step 401 the TEP amplitudes for all N electrodes of the group delivering TEPs are ramped up with an equal amplitude until for one electrode the activation threshold is reached. In step 402 the TEP amplitude for all N electrodes is reduced until below the activation threshold.

Following the above described rough titration close to threshold, the first TEP is presented to the patient at the first electrode and the amplitude is incremented to determine the activation threshold. The amplitude at the first electrode is increased until the specific activation threshold is reached (step 403). After the specific activation threshold is reached, for this specific electrode, the TEP amplitude is reduced until below the specific activation threshold (step 404). This is then repeated for each electrode. For that, step 405 asks whether there is another electrode (and repeats steps 403 and 404 if there is another electrode for TEP delivery). Finally, after all N electrodes are titrated, the so determined individual activation thresholds are used to set the TEP amplitude of each electrode independently.

Without losing generality, an embodiment of a therapy approach based on the novel multiphase stimulation waveform of the present invention, as presented in FIG. 5, is described for the treatment of chronic back and leg pain. Such therapy utilizes three (N=3) electrodes 102, namely 102.*a*, 102.*b*, and 102.*c* as shown in FIG. 5. Leads 101.*a* and 101.*b* are implanted and positioned so that electrodes 102.*a*, 102.*b*, and 102.*c* of one lead 101.*a* in the thoracic region may be utilized for therapy.

In the example the first therapeutic electric phase (therapeutic electric pulse) TEP of the novel multi-phase stimulation waveform is that of electrode 102.*c* (see obliquely striped pulse in FIG. 5) which delivers the first previously determined specific TEP amplitude by the first electrode 102.*c*. To implement it, the elements $I_{Pi}$ (see FIG. 2) of electrodes 102.*a* and 102.*b* are programmed to the desired specific amplitude I divided by 2 (=I/(N−1)) as charge balancing phases/pulses providing an anodic pulse (see pulses with checkerboard pattern). Electrode 102.*c* is connected to element $V_{NCounter}$ (see FIG. 2) in this therapeutic phase so the total current I provides cathodic stimulation at electrode 102.*c*.

One embodiment of charge balance, in at least one of the Inter-pulse Intervals IPI, is performed by closing switches 307 (see FIG. 2) for the participating electrodes 102.*a*-102.*c*. This avoids voltage runaway in the DC blocking capacitors $C_i$ of the mentioned electrodes that may be caused by mismatches in the generation of the different I/2(=I/(N−1)) among the different electrode drivers. It also keeps the electrode 102.*a*. 102.*b* and 102.*c* potentials within acceptable ranges for continuous therapy delivery.

One embodiment of timing parameters (see FIG. 5) are 30 μs and 140 μs, for the Pulse Width PW and Inter-pulse Intervals IPI respectively. This results in an equivalent frequency f, for the therapeutic phase at each electrode 102.*a*-102.*c*, slightly above 1,450 Hz. The PW example range is from 15 us to 1,000 us whereas that of IPI may start from tens of us to hundreds of μs or even a few thousand us.

The therapeutic phase amplitude I may be programmable in the order of less than 20.0 mA, preferably less than 10.0 mA, for example between 0.5 and 10.0 mA. The maximum charge injected in any therapeutic phase may be also limited by the IPG 104 to 10 μC to avoid tissue and electrode damage.

As explained above the IPG 104 comprises N=3 electrodes for TEP, each of the N electrodes undergoes a recurring pattern of an electrode specific therapeutic phase with a current amplitude I and a series of (N−1) charge balancing phases, which pass an inverted current amplitude I of the specific therapeutic phase delivered at the same time, for example distributed with equal weight (I/(N−1)). Each therapeutic phase TEP (see obliquely striped pulse in FIG. 5) is timely aligned with one charge balancing phase (see pulse with checkerboard pattern) of the other (N−1) electrodes such that in the cycle only one TEP occurs at one time. At the end of each stimulus cycle or in between, an additional charge balancing phase is used to compensate for residual electrode charge due to the amplitude variation with regard to each electrode (see pulses with cross-striped pattern). After every electrode cyclically-passed one TEP and the residual electrode charge compensation was provided in one additional phase (see first 4 columns showing amplitude levels of the electrodes in FIG. 5), the cycle starts again with the first of the N electrodes (see last column of FIG. 5 showing the amplitude levels for each electrode 102.*a*, 102.*b* and 102.*c*).

Hence, in the example using 3 active electrodes with the Rotating Electrodes therapy design the TEP (cathodic stimulation in the example) rotates across each individual electrode 102.*a*, 102.*b*, 102.*c* during each stimulation cycle while the remaining two electrodes serve as the anodic return. The TEP (cathodic) of each individual electrode 100 is balanced by its participation in two charge balancing pulses (anodic).

Now assume that the activation threshold on the top electrode 102.*c* for the first TEP is measured to be −4.0 mA (negative value represents a cathodic pulse). The second TEP corresponding to the middle electrode 102.*b* is then measured to be −6.0 mA. Finally, the activation threshold of the third TEP (bottom electrode 102.*a*) is measured to be −5.0 mA. For sub-perception therapy the stimulation amplitude is then programmed to 50% of activation threshold on each electrode corresponding to amplitudes of −2.0, −3.0, and −2.5 mA on the top electrode 102.*c*, middle electrode 102.*b* and bottom electrode 102.*a*, respectively. The programmed amplitudes for this example are listed in Table 1 (TEP amplitudes underlined). The residuals result in unbalanced electrodes 102.*b* and 102.*c*. By adding an additional charge balancing phase the residual charges can be balanced (right column).

TABLE 1

| Electrode | Amplitude (mA) 1st TEP | Amplitude (mA) 2nd TEP | Amplitude (mA) 3rd TEP | Amplitude (mA) Residual Charge Balancing Pulse |
|---|---|---|---|---|
| Top 102.c | −2.00 | 1.50 | 1.25 | −0.75 |
| Middle 102.b | 1.00 | −3.00 | 1.25 | 0.75 |
| Bottom 102.a | 1.00 | 1.50 | −2.50 | 0 |

This method is generalized for Rotating Electrodes (cathodes) using 3 electrodes in Table 2. The method further generalizes in a straightforward manner to 4 participating electrodes in the multi-phase novel SCS therapy.

TABLE 2

| Electrode | Amplitude (mA) 1st TEP | Amplitude (mA) 2nd TEP | Amplitude (mA) 3rd TEP | Amplitude (mA) Residual Charge Balancing Pulse |
|---|---|---|---|---|
| Top 100.c | −A | B/2 | C/2 | A − B/2 − C/2 |
| Middle 100.b | A/2 | −B | C/2 | −A/2 + B − C/2 |
| Bottom 100.a | A/2 | B/2 | −C | −A/2 − B/2 + C |

Now, the actual amplitudes of Table 2 may be impacted by current leakage present in the stimulation path. Hence, in one embodiment, besides driving the return currents X/2 (where X=A, B, or C depending on the TEP), each corresponding TEP electrode 102 is also actively driven with either amplitude A, B or C depending on the TEP. To implement this, the electrically-conductive area 303 of the case of the IPG 300 is used as a reference (auxiliary) active contact (see FIGS. 2 and 6). This embodiment can be thought as of simultaneous unipolar stimulation trains delivered against the electrically-conductive area of the IPG 300 case. Alternatively, another electrode 102 may be used as reference electrode instead of the electrically-conductive area 303.

In this embodiment therapy is delivered using a single lead 101.*a* as shown in FIGS. 3, 5 and 6 with preferred electrodes 102, namely electrodes 102.*a*, 102.*b*, and 102.*c*, and the different TEPs starting from electrode 102.*c*, moving to electrode 102.*a*, and repeating. Adjacent electrodes 102 on the same lead 101.*a* are shown for simplicity but electrodes 102.*a* to 102.*c* are not required to be adjacent. Similar arrangements can be conceived using dual percutaneous or paddle leads.

When the TEP is to be delivered in electrode 102.*c*, the current sink element of such electrode 102.*c* is programmed with amplitude A whereas the current source elements of electrodes 102.*b* and 102.*a* are simultaneously each programmed with amplitude A/2 in this embodiment example. The current difference $i_{Ref}$ (due to mismatch, finite impedance, etc.) between the actual current driving electrode 102.*c* and the sum of the currents driving electrodes 102.*a* and 102*b*, circulates through the electrically-conductive area 303. Trimming accuracy guarantees current $i_{Ref}$ is of such level that does not cause stimulation via the electrically-conductive area 303.

The delivery of the other TEPs in electrodes 102.*b* and 102.*a* can be described in an analogous manner to the instance when electrode 102.*c* delivers the TEP as described in the previous paragraph. As shown in FIGS. 2 and 6, the electrically-conductive area 303 also participates in the additional residual charge balancing phase circulating the difference in currents.

Besides programmable voltages $V_{IStim}$, from where current sources flow, and voltage $V_{NCounter}$ to where current sinks flow, this embodiment requires generating intermediate voltage $V_{Ref}$ that drives the electrically-conductive area 303. The circuitry that generates $V_{Ref}$ needs to have some driving capability for $i_{Ref}$ in the tens to hundred of $\mu_A$. Electrically-conductive are 303 is connected to $V_{Ref}$ via analog switch 203. Electrodes 102 can also be connected to $V_{Ref}$ via identical analog switches 203 (not shown in FIG. 2 for drawing simplicity).

In one embodiment of the neurostimulation device, outside of a clinic, automatic independent adjustment of TEP amplitudes may be provided. This may be accomplished with a modified, specific implementation of recording evoked compound action potentials (ECAPs) as follows.

The typical embodiment includes an implantable pulse generator (IPG) connected to one or more percutaneous or paddle leads 101 with multiple electrodes 102. To accurately program the variable TEP amplitudes to a sub-perception level, activation thresholds for each TEP must be measured separately using ECAPs. The first TEP is presented to the patient and the amplitude is incremented to determine the ECAP threshold 1, also called specific activation threshold 1, as shown in FIG. 7 which shows the activation signal plot, i.e. ECAP(μV) amplitude vs TEP amplitude I(mA). Point 1 in FIG. 7 is the perception threshold (PT) of the subject electrode (ECAP threshold), and point 2 is the first increment below the PT.

In one embodiment, titration and continued adjustment may proceed as follows (see FIG. 8). For each electrode 102, the PT level may be determined and recorded in the clinic according to FIG. 4 (for example for different body positions, see steps 401 to 405). Then, as indicated by step 406, the stimulation therapy is delivered until auto-adjust is desired. Then, the sensed ECAP amplitudes at PT may be recorded (target ECAP amplitudes) as well as the selected TEP amplitude relationship to the PT, for example (60%, or 0.4 mA below PT) using steps 407 to 411 of FIG. 8. TEPs may then be delivered at this selected amplitude.

On an interval basis, this amplitude could be adjusted automatically as follows: Upon completion of a stimulation cycle, the IPG 104 delivers a TEP at the PT level (step 407) to one electrode 102 and the resulting ECAP is measured (step 408). In step 409 the ECAP wave-form is assessed. If the ECAP is below the target ECAP amplitude, the stored PT level is incremented as well as the TEP amplitude. If the measured ECAP amplitude is above the target ECAP amplitude, these values would be decremented instead. In the next step 410 the TEP amplitude is set to below the activation threshold for the respective electrode 102. Then, in step 411 it is verified whether the titration is done for each of the N electrodes. If not, the procedure continues with step 407. If yes, the automatic TEP amplitude adjustment is finished. A design relationship is maintained between the PT and the TEP amplitude, and the latter will track the former in a deterministic manner.

In the following another embodiment of a multi-phase SCS therapy utilizing 3 electrodes 102.*a*. 102.*b* and 102.*c* as shown in FIGS. 9 to 11 is described. Therapy may be delivered leaving unused electrodes 110 in between therapeutic electrodes 102.*a*, 102.*b* and 102.*c*. When the bottom electrode 102.*a* is the therapeutic electrode in the rotation, an ECAP is present in signal 503 recorded from electrodes 102.*b* and 102.*c* via sensing front-end 502 contained in the IPG 104. Mismatches between the different electrode-tissue and nerve impedances, and sensing components, may be compensated via adjustment of the current sources flowing through the electrodes 102.*b* and 102.*c* (in this case) to have similar voltage profiles at the inputs of the sensing front-end 502. These signals are then seen as common mode by the latter, which can reject them by its high common mode rejection ratio (CMRR) specification. This results in a "recordable" stimulus artifact SA (i.e. sensing front-end 502 is not saturated and SA of amplitude comparable to the ECAP to be recorded). Recording may occur simultaneously with the delivery of the TEPs as multi-phase SCS therapy frequencies are typically substantially higher than frequencies used in traditional tonic SCS. Embodiments for the implementation of sensing front-end 502, and signal processing to reject and remove SA, are taught by U.S. Pat. No. 10,842,996 B2.

When the middle electrode 102.*b* is the therapeutic electrode in the rotation, auxiliary electrodes 200.*a* and 200.*b* (FIG. 10) are required for ECAP recording given the symmetry in the system (electrode 102.*b* is equidistant from electrodes 102.*a* and 102.*c*). Utilizing these auxiliary electrodes 200.*a* and 200.*b* however does not affect the ECAP signature when only electrodes 102.*b* and 102.*a*, 102.*c* participate in the rotation. As mentioned before, the IPG 104 hardware guarantees electrodes 200.*a* and 102.*c* undergo a similar voltage swing that can be rejected by the sensing front-end 502 high CMRR.

The balancing of charge through auxiliary electrodes 200.*a* and 200.*b* occurs during a residual charge balancing pulse as described in Table 3 below. The electrodes 102.*a*. 102.*b* and 102.*c* form the group of N electrodes (in this embodiment N=3) providing the therapeutic phases, whereas the electrodes 200.*a* and 200.*b* are additional electrodes which together with the group of N electrodes form the plurality of electrodes with the number Z (in this embodiment Z=N+2 =5).

The time when top electrode 102.*c* is the therapeutic electrode in the rotation is shown in FIG. 11. This case is analogous to the one shown in FIG. 9 (note that ECAPs propagate in both directions).

Utilizing the recorded ECAPs, amplitudes are set for each TEP at each rotating electrode 102.*a* to 102.*c*.

ECAPs sensing is not required to be performed on a cycle by cycle basis and may be triggered by circuitry (e.g. an accelerometer) in the IPG 104 when body position changes are detected as these will affect the distance between the electrodes 102 and fibers to be stimulated thus affecting the activation threshold. For example, when running multi-phase SCS therapy at 300 Hz, ECAP sensing can occur every 32 cycles. When ECAPs are sensed, the residual charges on the auxiliary electrodes 200.*a* and 200.*b* also need to be balanced during the residual charge balancing pulse. In this case, Table 2 changes to that shown in Table 3.

TABLE 3

| Electrode | Amplitude (mA) 1st Therapeutic Electric Pulse | Amplitude (mA) 2nd Therapeutic Electric Pulse | Amplitude (mA) 3rd Therapeutic Electric Pulse | Amplitude (mA) Residual Charge Balancing Pulse |
|---|---|---|---|---|
| Top 100.c | −A | B/4 | C/2 | A − B/4 − C/2 |
| Middle 100.b | A/2 | −B | C/2 | −A/2 + B − C/2 |
| Bottom 100.a | A/2 | B/4 | −C | −A/2 − B/4 + C |
| Auxiliary 200.a | 0 | B/4 | 0 | −B/4 |
| Auxiliary 200.b | 0 | B/4 | 0 | −B/4 |

The above embodiments of an inventive device and method use a similar multi-phase therapy with independent amplitudes in each therapeutic electric pulse, followed by a charge balancing phase which acts on the collection of active electrodes. This method improves neurostimulation therapy efficacy by allowing operator programming to account for threshold variation across the electrodes on one implanted lead. Further, a method is described to automatically adjust these amplitudes based on Evoked Compound Action Potentials (ECAPs) recording to maintain the amplitudes in an ideal therapeutic sub-perception window.

The invention claimed is:

1. A device for neurostimulation (100) of a patient's body, wherein the device comprises a plurality of electrodes (102.*a*, 102.*b*, 102.*c*, 102.*d*, 200.*a*, 200.*b*), wherein the number of the plurality of electrodes is Z, wherein a group of N electrodes (102.*a*, 102.*b*, 102.*c*) of the plurality of electrodes is equal to or larger than 3, wherein the device is configured to deliver a number of N+1 electrical phases during one cycle via the plurality of electrodes such that:

(a) during N electrical phases of the cycle each electrode of the group delivers alternating a therapeutic electric phase and a number of N−1 charge balancing electric phases, wherein the therapeutic electric phase of one electrode has an amplitude I1, I2, . . . IN specific to this electrode, wherein during a time of one phase one electrode of the group delivers its specific therapeutic electric phase and the other electrodes of the group or of the plurality of electrodes deliver a charge balancing phase having a polarity being opposite to the polarity of the specific therapeutic electric phase delivered at the same time; and (b) during an additional electrical phase each electrode of the plurality of electrodes delivers an electrical phase with an amplitude that establishes charge neutrality for residual charge on each respective electrode accumulated during the N electrical phases.

2. The device of claim 1, wherein the device is configured such that amount of the amplitudes of the charge balancing electric phases is the (N−1)th part or the (Z−1) th part of the amount of the specific amplitude of the specific therapeutic electric phase delivered at the same time during one of the N therapeutic electrical phases.

3. The device of claim 1, wherein the device is configured such that the amplitude of the specific therapeutic phase of each electrode of the group (102.*a*, 102.*b*, 102.*c*) is automatically adjusted using ECAP waveform measurement.

4. The device of claim 3, wherein the device is configured such that ECAP waveform measurement is provided using at least one auxiliary electrode (200.*a*, 200.*b*) of the plurality of electrodes Z (102.*a*, 102.*b*, 102.*c*, 102.*d*, 200.*a*, 200.*b*) different from the group of electrodes N (102.*a*, 102.*b*, 102.*c*).

5. The device of claim 3, wherein the device is configured such that the ECAP waveform measurement is provided in predefined time intervals and/or if the patient's body position and/or activity change is detected by using an accelerometer contained within the device.

6. The device of claim 1, wherein the device is configured such that for assessing the amplitude of the specific therapeutic electric phase of each electrode of the group N (102.*a*, 102.*b*, 102.*c*) the specific activation threshold (1) for each electrode is determined, wherein the amplitude of one specific electrode of the group is a pre-defined part of the measured specific activation threshold of this electrode.

7. The device of claim 1, wherein during any of the N+1 phases, the device casing sources or sinks current to provide balance to the net currents of the active electrodes.

8. The device of claim 1, wherein the group of N electrodes of the plurality of electrodes is a subset of electrodes of the plurality of electrodes.

9. A method for neurostimulation of a patient's body using a plurality of electrodes (102.*a*, 102.*b*, 102.*c*, 102.*d*, 200.*a*, 200.*b*), wherein the number of the plurality of electrodes is Z, wherein a group of N electrodes (102.*a*, 102.*b*, 102.*c*) of the plurality of electrodes (N less than or equal to Z) is equal to or larger than 3, wherein a number of N+1 electrical phases during one cycle via the plurality of electrodes is delivered, wherein during N electrical phases of the cycle each electrode of the group delivers alternating a therapeutic electric phase and a number of N−1 charge balancing electric phases, wherein the therapeutic electric phase of one electrode has an amplitude I1, I2, . . . IN specific to this electrode, wherein during a time of one phase one electrode of the group delivers its specific therapeutic electric phase and the other electrodes of the group or of the plurality of electrodes deliver a charge balancing phase having a polarity being opposite to the polarity of the specific therapeutic phase delivered at the same time; and wherein during an additional electrical phase each electrode of the plurality of electrodes delivers an electrical phase with an amplitude that establishes charge neutrality for residual charge on each respective electrode accumulated during the N electrical phases.

10. The method of claim 9, wherein the amount of the amplitudes of the charge balancing electric phases is the (N−1)th part or the (Z−1)th part of the amount of the specific amplitude of the specific therapeutic electric phase delivered at the same time during one of the N electrical phases.

11. The method of claim 9, wherein the amplitude of the specific therapeutic phase of each electrode of the group (102.*a*, 102.*b*, 102.*c*) is automatically adjusted using ECAP waveform measurement.

12. The method of claim 11, wherein the ECAP waveform measurement is provided using at least one auxiliary electrode (200.*a*, 200.*b*) of the plurality of electrodes (102.*a*, 102.*b*, 102.*c*, 102.*d*, 200.*a*, 200.*b*) different from the group of electrodes (102.*a*, 102.*b*, 102.*c*).

13. The method of claim 11, wherein the ECAP waveform measurement is provided in predefined time intervals and/or if the patient's body position and/or activity change is detected by using an accelerometer contained within the device.

14. The method of claim 9, wherein for assessing the amplitude of the specific therapeutic phase of each electrode of the group (102.*a*, 102.*b*, 102.*c*) the specific activation threshold (1) for each electrode is determined, wherein the amplitude of one specific electrode of the group is a predefined part of the measured specific activation threshold of this electrode.

15. A neurostimulation system, comprising:

at least one implantable lead comprising a plurality of electrodes; and an implantable pulse generator (IPG) electrically coupled to the at least one implantable lead, wherein the IPG comprises control circuitry configured to generate a stimulation cycle comprising N+1 electrical phases, wherein N is a group of electrodes of the plurality of electrodes equal to or larger than 3;

wherein during N electrical phases of the cycle, the control circuitry causes each electrode of the group to deliver alternating a therapeutic electric phase and a number of N−1 charge balancing electric phases, wherein the therapeutic electric phase of one electrode has an amplitude specific to this electrode, and wherein during a time of one phase one electrode of the group delivers its specific therapeutic electric phase and the other electrodes of the group or of the plurality of electrodes deliver a charge balancing phase having a polarity being opposite to the polarity of the specific therapeutic electric phase delivered at the same time; and wherein during an additional electrical phase, the control circuitry causes each electrode of the plurality of electrodes to deliver an electrical phase with an amplitude that establishes charge neutrality for residual charge on each respective electrode accumulated during the N electrical phases.

16. The neurostimulation system of claim 15, wherein the IPG further comprises sensing circuitry configured to record an evoked compound action potential (ECAP) via at least one of the plurality of electrodes, and wherein the control circuitry is configured to automatically adjust the amplitude of the therapeutic electric phase of at least one electrode of the group based on the recorded ECAP.

17. The neurostimulation system of claim 16, wherein the sensing circuitry is configured to record the ECAP using at least one auxiliary electrode of the plurality of electrodes that is distinct from the group of N electrodes delivering the therapeutic electric phases to minimize stimulation artifact.

18. The neurostimulation system of claim 15, wherein the IPG further comprises a plurality of bleeding resistors and a plurality of switches, and wherein during the additional electrical phase, the control circuitry is configured to operate the plurality of switches to connect the plurality of electrodes to the bleeding resistors to provide passive charge balancing.

19. The neurostimulation system of claim 15, wherein the control circuitry is configured to deliver the therapeutic electric phases with amplitudes established below a perception threshold of the patient to provide paresthesia-free neurostimulation.

20. The neurostimulation system of claim 15, further comprising an external programmer configured to wirelessly communicate with the IPG.

* * * * *